Figure 1:
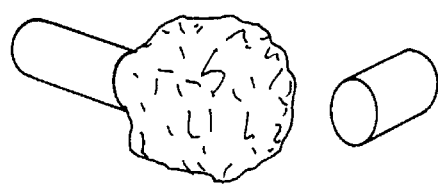
Figure 2:
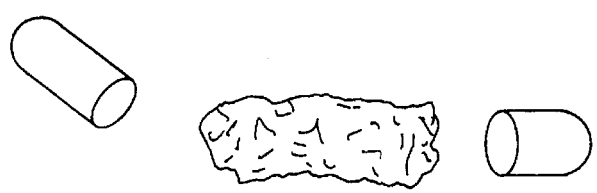
Figure 3:
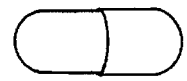
Figure 4:
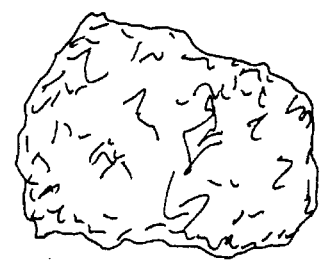

United States Patent

Ratjen et al.

Patent Number: 5,603,950
Date of Patent: Feb. 18, 1997

[54] AGENT FOR ORAL INTAKE

[76] Inventors: Werner Ratjen, Freeweid 12-14, D-2302 Flintbek; Hans R. Willmen, Nachtigallenstasse 22, D-4048 Grevenbroich, both of Germany

[21] Appl. No.: 336,330

[22] Filed: Nov. 7, 1994

Related U.S. Application Data

[63] Continuation-in-part of Ser. No. 20,665, Feb. 22, 1993, abandoned, which is a continuation-in-part of Ser. No. 744,985, Aug. 14, 1991, abandoned.

[30] Foreign Application Priority Data

Aug. 14, 1990 [DE] Germany .................. 40 25 912.41

[51] Int. Cl.⁶ ...................................................... A61K 9/48
[52] U.S. Cl. .................. 424/451; 424/453; 424/452; 514/962; 514/777; 514/772.3; 514/781; 514/911

[58] Field of Search ..................... 424/451, 452, 424/456, 453; 514/909, 910, 911

[56] References Cited

U.S. PATENT DOCUMENTS 3,688,763  9/1972  Cromarty ................................ 128/2 B
4,609,403  9/1986  Wittwer et al. ......................... 106/122

Primary Examiner—James M. Spear
Attorney, Agent, or Firm—Dvorak and Traub

[57] ABSTRACT

The drug consists of a two-part gelatine capsule filled with a non-toxic substance, low on burnable ingredients, which enlarges its volume when set free in the stomach. The filling can be dissolved within the digestive tract of the human body, e.g. compressed cellulose. The person taking the drug experiences through the volume enlargement in the stomach for a certain time a feeling of fulness, hencely making it easier to lose weight.

8 Claims, 1 Drawing Sheet

AGENT FOR ORAL INTAKE

This application is a continuation-in-part of application Ser. No. 08/020,665 filed 22 Feb. 1993, now abandoned, which is a continuation-in-part of application U.S. Ser. No. 07/744,985 filed on Aug. 14, 1991 now abandoned.

The invention a) refers to an oral agent in a capsule which will dissolve in the stomach and set the content free b) provides the method to produce such an agent.

There have been numerous attempts to decompose or so prevent the formation of superfluous depositions of fat in the human body. These depositions can be observed nowadays in many persons as a kind of civilizational disease. There are so called "appetite curbers" which try with biochemical means to suggest to the body a dislike towards eating (lack of appetite). Some of these drugs have several harmful side affects.

Besides many known diet proposals there are also mechanical and electro mechanical means which are supposed to achieve a reduction of fat or a muscle building respectively. The effect of such means are very much in doubt.

The simple reduction of food intake requires a degree of self-control which many people are not able to muster up in the long run.

The invention deals with the task to create a product for weight reduction which a) avoids the above mentioned drawbacks, especially the regularly occurring side affects of the "appetite curbers" b) is easy to apply, c) is inexpensive in its production, d) can be unproblematically applied without medical assistance.

Furthermore a method for the production of such a product shall be created.

The invention solves the problem at hand through an oral agent, which consists of a capsule and its content, and is preferably a two-part soluble gelatin capsule. The capsule dissolves in the stomach and hencely sets free the nontoxic substance which is volume-enlarging and low in caloric content. The substance will disintegrate within the digestive tract or evacuate the bowels.

The methodical part of the task is being solved by the properties described in claim 8. The properties described in the sub-claims constitute an advantageous further development of the invention.

The invention creates a product which fills the stomach by volume and hencely suggests to the body the feeling of fullness. The substance in this agent is a digestible sponge material selected in a way that it is, in regard to its free volume, extremely low on material usable for body-building. It is also easily digestible. The substance should have a physically cohesive structure, and should be compressible so that it may be disposed within the capsule. After being set free in the stomach, the compressed substance should have the ability to expand considerably, preferably to a multiple of its original volume, and absorb fluids, wherein the expanded substance should retain its physically cohesive structure and does not immediately pass into the following digestive tract, but remains in the stomach to promote a temporary sensation of fullness. In addition the substance must be soluble in the human digestive tract or disposable by bowel evacuation. Such substances are known and indicated among the sub-claims. Usable are for example polyurethane foam or cellulose (as natural substance) or other suitable substances.

Cellulose foam with a density of 0.01 kg/dm$^3$ to 0.05 kg/dm$^3$ has proven itself especially successful. Preferred is here a foam consisting of alveolar cellulose, reinforced by natural fiber, e.g. cutton alveolar cellulose is cellulose made of wood pulp. This cellulose foam can, when filled into a capsule—especially a gelatin capsule—be wound or compressed highly. This substance is—as far as known up to now—completely without danger for the human body and is being dissolved slowly so that the effect of a product, filled with this substance, lasts relatively long.

The product described herein may be enriched with vitamins and mineral substances for food supplement for use in connection with a reducing diet.

1. During a reducing diet, the body suffers from a deficiency in necessary vitamins and minerals. This deficiency may be compensated by the product described herein.

2. The food supplement products (fiber ballast substances) contained in this product dull the sense of hunger, so that less food is eaten. It is thereby possible to individually control your food intake in the sense of the "FDH" principle. This is the most logical and most natural method of weight reduction.

Gelatin, (cellulose), grain milling products, emulsifier, vegetable protein, vitamin C, vitamin E, calcium, potassium, and magnesium may all be included in the product.

Amino acids may also be included for the supplementation of the daily protein requirement.

The cellulose processed in the product is a vegetable fiber rich in ballast substance and is chemically pure. Use of the product causes the absorption of carbohydrates to be delayed. Also, blood sugar rise and the insulin fall-out are reduced, and digestion is promoted.

Grain milling products may consist of rye, full grain loosened, with sourdough, baked gently in saturated steam, dried and ground. These elements are digestion-stimulating.

Vegetable protein with valuable essential amino acids may also be included.

Vitamins are vitally important.

Health, well-being and initiative are only achieved where there is a significient supply of all vitamins.

Our body cannot produce vitamins independently. They must be supplied daily.

Vitamin C prevents scurvy, promotes cell respiration, glandular functioning, resistance to infection, detoxification, blood formation, sealing of the blood vessels of the teeth, and bone formation.

Vitamin E supports and stabilizes the body cells, prevents deficiency ailments and functional disturbances of the pancreatic fluid gland and gall bladder. Regulation of the metabolism is also achieved.

Calcium is necessary not only for building bones and cells but also for the entire metabolism in the body.

Calcium which is supplied to the body by foods does not always suffice to cover the requirements.

Calcium salts give bones and teeth their strength.

Potassium is active in the regulation of the osmotic pressure within the cell.

Potassium is a component of the digestive fluid of the gastric and intestinal tract. It is rapidly resorbed.

Magnesium is important for the muscular functions. Magnesium is an essential nutrient which occurs in nearly all cells and is involved with activation of enzymes with respect to the energy metabolism.

The vitamins and mineral substances contained in this product cover, according to recommendation of the DGE (German Association for Nutrition), the daily requirement for the corresponding vitamins and mineral substances if 20 capsules per day are ingested.

| Nutritive value data, average analysis | | |
| --- | --- | --- |
| | 1000 capsuls of 1 g ea (= 1000 g) contain | 1 capsule contains |
| Fat | 1 g | Traces |
| Protein | 470 g | 0.5 g |
| Carbohydrates | 35 g | Traces |
| Average physiological combustion value | 8736 KJ 2080 Kcai | 8.4 KJ 2.1 Kcal |

Intake recommendation per day is 4×5 capsules half an hour before food intake.

As mentioned above other suitable substances can be used instead of cellulose, e.g. polyurethane foam. In that case it is advantageous to use a foam with a density of less than 0.025 kg/dm³.

In order to achieve that the process of volume enlargement takes place not before the drug is in the stomach, it is necessary to fill the substance into a container which is being dissolved in the stomach, at least is there destroyed. For practical reasons customary gelatine capsules are being used. They a) have enough mechanical stability in order to hold the substance in its compressed form b) can be manufactured cheaply and c) are being used successfully for years.

The materials described above, as is known, are easily digestible. The production costs are very favorable. Proper or improper use by children prove nonproblematical.

Technically it constitutes a certain problem to compress the filling and to insert it in this compressed form into the capsule or to compress the filling directly in the container itself. The invention provides for this task a procedure as is described in claim 8. This procedure is especially suited for the use of polyurethane foam or cellulose foam as active substance. Nevertheless this procedure can be used also with other substances. The filling must be wound or pressed highly before being inserted into the container. This way the filling is being compressed, and reduced to a fraction of its free volume. The compressed filling is then inserted into (the) one part of the two-part capsule. At the end of the procedure the substance-filled part is being closed by the overlapping second part in a way as is commonly known. In preliminary testing this method has been especially successful because it allows a very high compression of the filling and is also applicable in large-scale industry.

I claim:

1. An orally ingestible product comprising a soluble capsule and an expandable, digestible cohesive sponge material comprised of a grain milling product of wheat fiber of substantially negligible caloric and nutritional content and disposable in a compressed form in said soluble capsule, said digestible sponge material of wheat fiber being expandable to a multiple of the capsule volume upon dissolution of the soluble capsule in a stomach of an ingestor, wherein said expanded sponge material of wheat fiber does not immediately pass from the stomach into a digestive tract, but remains in the stomach to promote a temporary sensation of fullness.

2. An orally ingestible product comprising a soluble capsule and an expandable, digestible cohesive sponge material selected from the group consisting of emulsifiers, vegetable protein, vitamins, and minerals of substantially negligible caloric and nutritional content and disposable in a compressed and freeze-dried form in said soluble capsule, said digestible sponge material being expandable to a multiple of the capsule volume upon dissolution of the soluble capsule in a stomach of an ingestor, wherein said expanded sponge material does not immediately pass from the stomach into a digestive tract but remains in the stomach to promote a temporary sensation of fullness.

3. An orally ingestible product comprising a soluble capsule and an expandable, digestible cohesive sponge material of substantially negligible caloric and nutritional content and disposable in a compressed string-shaped form in said soluble capsule, said digestible sponge material being expandable to a multiple of the capsule volume upon dissolution of the soluble capsule in a stomach of an ingestor, wherein said expanded sponge material does not immediately pass from the stomach into a digestive tract, but remains in the stomach to promote a temporary sensation of fullness.

4. An orally ingestible product comprising a soluble capsule and an expandable digestible cohesive sponge material comprised of cellulose foam with a density from 0.01 kg/dm³ to 0.05 kg/dm³ of substantially negligible caloric and nutritional content and disposable in a compressed form in said soluble capsule, said digestible sponge cellulose material being expandable to a multiple of the capsule volume upon dissolution of the soluble capsule in a stomach of an ingestor, wherein said expanded sponge material cellulose foam does not immediately pass from the stomach into a digestive tract, but remains in the stomach to promote a temporary sensation of fullness.

5. An orally ingestible product comprising a soluble capsule and an expandable, digestible cohesive sponge material comprised of a cellulose foam of alveolar cellulose with a density from 0.01 kg/dm³ to 0.05 kg/dm³ of substantially negligible caloric and nutritional content and disposable in a compressed form in said soluble capsule, said digestible sponge material alveolar cellulose foam being expandable to a multiple of the capsule volume upon dissolution of the soluble capsule in a stomach of an ingestor, wherein said expanded sponge material alveolar cellulose foam material does not immediately pass from the stomach into a digestive tract, but remains in the stomach to promote a temporary sensation of fullness.

6. An orally ingestible product comprising a soluble capsule and an expandable, digestible cohesive sponge material of polyurethane foam having a density less than 0.025 kg/dm³ of substantially negligible caloric and nutritional content and disposable in a compressed form in said soluble capsule, said digestible sponge material polyurethane foam being expandable to a multiple of the capsule volume upon dissolution of the soluble capsule in a stomach of an ingestor, wherein said expanded sponge material polyurethane foam does not immediately pass from the stomach into a digestive tract, but remains in the stomach to promote a temporary sensation of fullness.

7. A method for manufacturing an orally ingestible product comprising the steps of separating an expandable, digestible and cohesive sponge material of substantially negligible caloric and nutritional content into string-shaped pieces, compressing said pieces, inserting said pieces into a first part of a soluble capsule, and enclosing said pieces by fastening a second part of a soluble capsule to said first part of a soluble capsule, wherein the sponge material is expandable in the stomach of an ingestor to promote a temporary sensation of fullness, and does not immediately pass onto the digestive tract.

8. A method for suppressing appetite comprising the steps of separating an expandable, digestible and cohesive sponge material of substantially negligible caloric and nutritional content into string-shaped pieces, compressing said pieces, inserting said pieces into a first part of a soluble capsule, and enclosing said pieces by fastening a second part of a soluble capsule to said first part of a soluble capsule, ingesting said capsule, dissolving said capsule, expanding said expandable digestible and cohesive sponge in the stomach of the ingestor to create the temporary sensation of fullness, and then digesting and eliminating said capsule and contents, wherein the sponge material does not immediately pass onto the digestive tract.

* * * * *